(12) United States Patent
Zhang et al.

(10) Patent No.: US 12,201,398 B2
(45) Date of Patent: Jan. 21, 2025

(54) MLA-OCT IMAGING CATHETER, MLA-OCT IMAGING SYSTEM AND MLA-OCT IMAGING METHOD

(71) Applicant: SUZHOU ARGUS MEDICAL TECHNOLOGY CORP LTD, Jiangsu (CN)

(72) Inventors: Lintao Zhang, Jiangsu (CN); Zhenying Wu, Jiangsu (CN); Qingyu Feng, Jiangsu (CN)

(73) Assignee: SUZHOU ARGUS MEDICAL TECHNOLOGY CORP LTD, Jiangsu (CN)

( * ) Notice: Subject to any disclaimer, the term of this patent is extended or adjusted under 35 U.S.C. 154(b) by 711 days.

(21) Appl. No.: 17/440,431

(22) PCT Filed: Mar. 25, 2020

(86) PCT No.: PCT/CN2020/081163
§ 371 (c)(1),
(2) Date: Sep. 17, 2021

(87) PCT Pub. No.: WO2020/192699
PCT Pub. Date: Oct. 1, 2020

(65) Prior Publication Data
US 2022/0160231 A1    May 26, 2022

(30) Foreign Application Priority Data

Mar. 26, 2019 (CN) .......................... 201910233461.6
Apr. 3, 2019 (CN) .......................... 201910266219.9

(51) Int. Cl.
*A61B 5/00* (2006.01)
*A61B 1/07* (2006.01)

(52) U.S. Cl.
CPC .............. *A61B 5/0044* (2013.01); *A61B 1/07* (2013.01); *A61B 5/0066* (2013.01); *A61B 5/6852* (2013.01)

(58) Field of Classification Search
CPC ........ A61B 1/07; A61B 5/0066; A61B 5/6852
See application file for complete search history.

(56) References Cited

U.S. PATENT DOCUMENTS

2002/0076178 A1* 6/2002 Klocek .............. G02B 23/2423
                                                        385/33
2005/0251116 A1* 11/2005 Steinke ................ A61B 5/0066
                                                        606/14
(Continued)

FOREIGN PATENT DOCUMENTS

CN          1780584        5/2006
CN        101247753        8/2008
(Continued)

OTHER PUBLICATIONS

âMicromachine phase-shifted array-type Mirau interferometer for swept-source OCT imaging: design, microfabrication and experimental validationâ by C. Gorecki et al. Biomedical Optics Express 1111. vol. 10, No. 3. Mar. 1, 2019. (Year: 2019).*

(Continued)

*Primary Examiner* — Jason M Ip
(74) *Attorney, Agent, or Firm* — Wenderoth, Lind & Ponack, L.L.P.

(57) ABSTRACT

An MLA-OCT imaging catheter (3), which comprises an inner tube (5), an outer tube (4) and a multi-core catheter connector (6), wherein the inner tube (5) comprises an optical fiber bundle (21) and a microlens array (7); a calibration method of the MLA-OCT imaging catheter; an MLA-OCT imaging system; and an imaging method thereof.

10 Claims, 3 Drawing Sheets

(56) References Cited

U.S. PATENT DOCUMENTS

| | | |
|---|---|---|
| 2006/0103850 A1 | 5/2006 | Alphonse et al. |
| 2007/0065080 A1 | 3/2007 | Camus et al. |
| 2008/0021276 A1 | 1/2008 | Wax |
| 2010/0290059 A1 | 11/2010 | Inoue |
| 2012/0158015 A1 | 6/2012 | Fowler et al. |
| 2016/0357007 A1 | 12/2016 | Swanson |
| 2018/0084981 A1 | 3/2018 | Wang |

FOREIGN PATENT DOCUMENTS

| | | |
|---|---|---|
| CN | 104739377 | 7/2015 |
| CN | 204500629 | 7/2015 |
| CN | 104854423 | 8/2015 |
| CN | 205215191 | 5/2016 |
| CN | 107752985 | 3/2018 |
| CN | 109893099 | 6/2019 |
| WO | 2004/096049 | 11/2004 |
| WO | 2006/133030 | 12/2006 |
| WO | 2014/088650 | 6/2014 |

OTHER PUBLICATIONS

International Search Report issued Jun. 15, 2020, in International (PCT) Application No. PCT/CN2020/081163, with English translation.
Extended European Search Report issued Mar. 23, 2022, in corresponding European Patent Application No. 20779952.9.

* cited by examiner

MLA-OCT IMAGING CATHETER, MLA-OCT IMAGING SYSTEM AND MLA-OCT IMAGING METHOD

TECHNICAL FIELD

The invention relates to the technical field of medical endoscopy detection, in particular to an MLA-OCT imaging catheter, an MLA-OCT imaging system and an MLA-OCT imaging method.

BACKGROUND ART

Coronary artery disease is the number one cause of death worldwide. Due to the accumulation, rupture and thrombosis of atherosclerotic plaques, coronary artery disease may cause chest pain (angina), myocardial ischemia and sudden cardiac death. For those patients without sudden death or with symptoms of chronic angina, suitable plaque treatments include PCI (Percutaneous Coronary Intervention). Cardiac intervention experts use PCI operation to place stents to deal with lesions. However, in recent years, many studies have concluded that cardiac stents have been abused or at least overused, which has caused a lot of controversy. Doctors are more cautious and critical when considering only using stents. In addition, since lower-cost drug treatments have been introduced to the market and they are found to be also effective by studies, in the treatment of stable coronary heart disease patients, we have seen a mild decline in stent implantation. However, currently three new vascular imaging/measurement equipment and consumables: 1) intravascular ultrasound, 2) OCT (Optical Coherence Tomography), and 3) fractional flow reserve technology, may accurately help doctors assess whether or not to place a stent for each patient before surgery and assess after surgery, and they play an increasingly important role in the examination of coronary heart disease.

The existing commercial intravascular IV-OCT (Intravascular Optical Coherence Tomographic) imaging system comprises a host equipment, an imaging catheter, and a retracement controller connecting the two, wherein the proximal end of the retracement controller is connected to an interferometer through an optical fiber, and the distal end is connected to the imaging catheter through a catheter connector. The host equipment comprises a laser, an interferometer, a photodetector, a data acquisition card, an imaging host, an image processor and a display terminal, wherein the interferometer carries the most core components of the imaging system: the left side of the interferometer is the laser input, the right side is the optical signal output, the upper part is the reference arm comprising a variable optical delay line (VODL), and the lower part is the signal arm comprising a retracement controller and an imaging catheter.

The reference arm of the interferometer of the existing IV-OCT imaging system has a variable optical delay line, and the signal arm has an imaging catheter and a retracement controller; wherein the retracement controller has a stepping motor for controlling the retracement, and a servo motor for controlling high speed rotation, and an optical fiber slip ring. The core of OCT imaging technology is to use the imaging catheter located on the signal arm of the interferometer to emit laser and collect the scattered light returned from the human tissue, which interferes with the optical signal of the reference arm of the interferometer for coherent detection; the imaging host generates a lumen image based on detecting the envelop of the interference signal. The optical path of the reference arm must be very close to the actual optical path of the signal arm in order to obtain high-quality coherent detection. In actual products, the length of different imaging catheters will be slightly different, so the OCT system has a variable optical delay line on the reference arm of the interferometer. According to the optical path change caused by different catheter lengths on the signal arm, the reference arm adjusts the optical delay line for matching so as to ensure the best interference performance. Herein, the main optical paths of the reference arm and the signal arm are both a single optical fiber, corresponding to a single microlens at the head end of the inner tube of the imaging catheter. The scanning around the lumen is completed by the high-speed rotation of a single microlens driven by the servo motor and the optical fiber slip ring in the retracement controller, and the torque sleeve outside the inner tube of the imaging catheter.

The specific imaging process of the IV-OCT imaging system includes: sending the imaging catheter along the guiding wire to the distal end of the intravascular lesion, which exceeds the lesion area by more than 5 mm, and then activating the imaging catheter by the retracement controller to retract and retreat, so as to scan the entire lesion area. The retracement process generally lasts 1-7 seconds, and the retracement distance is 50-150 mm. During this period, the outer tube of the imaging catheter does not move, the servo motor (i.e., rotating motor) and linear motor (i.e., stepping motor) of the retracement controller control the inner tube of the imaging catheter to retreat while rotating at high speed, so as to perform spiral point scanning of the blood vessel tissue and collect the scattered optical signals returned from each point of the blood vessel tissue; when the inner tube retreats to the presetting retracement distance of the product (such as 50 mm), the two motors stop and the scanning is completed, and the host equipment generates a complete image of the vascular tissue lesion according to the detected scattered optical signals returned from each point.

The imaging catheter realizing this IV-OCT imaging method comprises an outer tube, an inner tube, and a catheter connector; wherein the inner tube comprises an optical fiber and a microlens, and a torque sleeve is provided outside the optical fiber; the Rapid Exchange (Rx) tip design commonly used for PCI interventional surgical catheters is adopted for the distal end of the outer tube. The doctor first puts a guiding wire from the quick exchange tip through the imaging catheter outside the patient's body, and then pushes the imaging catheter to the target lesion area along the guiding wire in the patient's blood vessel. When performing OCT imaging, the outer tube of the imaging catheter does not move, and the guiding wire through the quick exchange tip does not move, only the inner tube rotates at a high speed and retreat. If the inner tube does not rotates evenly and smoothly, it may collide and rub against the inner wall of the outer tube, causing the outer tube to shake, which will drive the guiding wire at the quick exchange tip of the outer tube to shake; in severe cases, the guiding wire may become entangled with the imaging catheter and hurt the patient. This is a potential safety risk of current products.

Secondly, because this commercial IV-OCT imaging method is based on mechanically rotating a microlens to scan the luminal tissue laterally, it must ensure that the microlens at the distal end of the imaging catheter rotates evenly to obtain accurate images without distortion. The process includes: the high-speed rotation of the servo motor located in the retracement controller causes the torque sleeve outside the inner tube of the imaging catheter to drive the high-speed rotation of the distal microlens, thereby driving the high-speed rotation of the microlens' scanning beam to realize the laterally scanning of the target tissue around the lumen, at the same time, collecting the scattered light returned from the corresponding target tissue around the lumen at high speed. The generation of accurate image is based on precise synchronization of the rotation speed of microlens, the rotation speed of servo motor, and the frequency sweep speed of light source; if the rotation of the proximal motor is not synchronized with the rotation of light spot of the lens, the image will be distorted. Because the catheter follows the natural lumens of the human body, including but not limited to blood vessels, when approaching the lesion area in the body, these lumens have different shapes and bends; the bent imaging catheter is easy to cause the unsynchronized rotation of the distal and proximal ends of the imaging catheter. Therefore, image distortion is a major challenge for the accuracy of intraluminal IV-OCT imaging.

CONTENTS OF THE INVENTION

As mentioned above, if the inner tube of the OCT imaging catheter in the prior art does not rotates evenly and smoothly, it may collide and rub against the inner wall of the outer tube, causing the outer tube to shake, which will drive the guiding wire at the quick exchange tip of the outer tube to shake; in severe cases, the guiding wire may become entangled with the imaging catheter and hurt the patient. In addition, the bent imaging catheter is easy to cause the unsynchronized rotation of the distal and proximal ends of the imaging catheter, thereby resulting in distortion of the image obtained by the intraluminal IV-OCT imaging.

In order to solve the above problems, the main object of the present invention is to provide a novel intraluminal optical coherence tomography imaging method (MLA-OCT, microlens array optical coherence tomography), which completely eliminates the rotational movement of inner tube of imaging catheter which is necessary for the current commercial intraluminal IV-OCT imaging method, so as to reduce the risk of injury to the patient during the retracement process of the imaging catheter, and avoid image distortion caused by the unsynchronized rotation of the distal and proximal ends of the imaging catheter.

In order to achieve the above object, the technical solutions provided by the present invention are as follows:

In the first aspect of the present invention, provided is an MLA-OCT imaging catheter, comprising an inner tube, an outer tube and a multi-core catheter connector, wherein
  the inner tube is located inside the outer tube;
  the inner tube comprises an optical fiber bundle and a microlens array, the optical fiber bundle comprises two or more optical fibers, the microlens array comprises two or more microlenses, and the microlens array is located at the distal end of the optical fiber bundle;
  the proximal end of the outer tube is connected to a retracement controller for driving the retracement of the MLA-OCT imaging catheter through a multi-core catheter connector.

In the above MLA-OCT imaging catheter, the distal end of the outer tube is provided with a quick exchange tip, and the quick exchange tip is provided with a developing ring and a guiding wire inlet and outlet.

In the above MLA-OCT imaging catheter, the distal end of the outer tube is provided with a transparent imaging window.

In the above MLA-OCT imaging catheter, the multi-core catheter connector is provided with anti-slip lines.

According to another aspect of the present invention, provided is an MLA-OCT imaging system, comprising: a host equipment, a retracement controller, and the aforementioned MLA-OCT imaging catheter, wherein:
  the host equipment comprises an optical device and a data processing device, the optical device comprises a light source and an interferometer; the signal arm of the interferometer is provided with a retracement controller and an MLA-OCT imaging catheter, and the reference arm of the interferometer is provided with an optical delay line; the light source is divided into a beam of sample light and a beam of reference light by the interferometer, the sample light enters the signal arm of the interferometer to reach human tissue, and the multi-point scattered light returned from human tissue and collected by the MLA-OCT imaging catheter is a set of scanning optical signals, wherein each single-point scattered light is a first optical signal, and the scanning optical signal is a collection of the first optical signals of each single point; the reference light enters the reference arm of the interferometer to reach the optical delay line of the interferometer, and the light returned by the optical delay line is the second optical signal; wherein the first optical signal and the second optical signal return to the interferometer to interfere to generate an interference signal which is then sent to the data processing device;
  the retracement controller comprises a stepping motor, a first high-speed optical switch, an optical fiber bundle, and an optical fiber array connector; the proximal end of the retracement controller is connected to the interferometer, and the distal end is connected to the MLA-OCT imaging catheter through a multi-core catheter connector, the MLA-OCT imaging catheter is activated by the retracement controller to move axially to perform axial scanning, so as to generate a three-dimensional image of the tissue.

In the above MLA-OCT imaging system, the data processing device comprises: a photodetector, a data acquisition card, an imaging host, an image processor, and a display terminal.

In the above MLA-OCT imaging system, the host equipment comprises a closed-loop monitoring device for retracement.

In the above MLA-OCT imaging system, the reference arm is provided with a second high-speed optical switch and an optical delay line array comprising two or more optical delay lines; optionally, the reference arm is provided with one optical delay line.

According to another aspect of the present invention, provided is a method for calibrating the MLA-OCT imaging catheter in the above MLA-OCT imaging system, including: after connecting an MLA-OCT imaging catheter comprising an optical fiber bundle to a retracement controller, adjusting the position of the corresponding optical delay line on the reference arm for each optical fiber by a data processing device according to the signal-to-noise ratio of the received interference signal until the signal-to-noise ratio is the highest, at this time the value of the delay time for the optical delay line of each optical fiber is the calibration value of the optical delay line.

According to still another aspect of the present invention, provided is an MLA-OCT imaging method using the above MLA-OCT imaging system, which includes the following steps:

connecting the MLA-OCT imaging catheter to the retracement controller through a multi-core catheter connector;

dividing the light source into a beam of sample light and a beam of reference light by an interferometer, wherein the sample light enters the signal arm of the interferometer to reach human tissue, and the multi-point scattered light returned from human tissue and collected by the MLA-OCT imaging catheter is a set of scanning optical signals, and wherein each single-point scattered light is a first optical signal, and the scanning optical signal is a collection of the first optical signals of each single point; the reference light enters the reference arm of the interferometer to reach the optical delay line of the interferometer, and the light returned by the optical delay line is the second optical signal; wherein the first optical signal and the second optical signal return to the interferometer to interfere to generate an interference signal which is then sent to the data processing device;

adjusting the position of the corresponding optical delay line on the reference arm for each optical fiber by a data processing device according to the signal-to-noise ratio of each received interference signal until the signal-to-noise ratio is the highest, at this time the value of the delay time for the optical delay line of each optical fiber is the calibration value of the optical delay line which is stored in the MLA-OCT imaging system;

automatically setting the arm length of the reference arm by the MLA-OCT system based on the pre-stored calibration value of the optical delay line, so as to detect the interference signal, wherein the data processing device generates a two-dimensional lumen cross-section image of the human tissue based on all the detected interference signals; and actuating the MLA-OCT imaging catheter to move axially by the retracement controller to perform axial scanning, so as to generate a three-dimensional image of the human tissue.

The Benefit Effect of the Invention

The invention adopts microlens array, optical fiber bundle, optical fiber array connector, optical delay line array and high-speed optical switch to realize multi-point imaging signal acquisition, so that the MLA-OCT imaging catheter may acquire the scanning optical signal of the multi-point scattered light from the two-dimensional cross section of the lumen without high-speed rotation, thereby generating a tomographic image of the lumen. Compared with the prior art, the rotation movement of the inner tube of the imaging catheter is omitted in the present invention, thereby simplifying the OCT imaging process of the lumen, greatly improving the safety of the intraluminal imaging process, and reducing the risk of injury to the patient by the imaging catheter during the imaging process. In addition, since the MLA-OCT imaging catheter does not have high-speed rotation movement, it also completely eliminates the phenomenon of image distortion caused by the unsynchronized rotation of the proximal and distal ends of the imaging catheter.

| Symbol Description |
| --- |
| 1: Host equipment |
| 2: Retracement controller |
| 3: MLA-OCT imaging catheter |
| 4: Outer tube |
| 5: Inner tube |
| 6: Multi-core catheter connector |
| 7: Microlens array |
| 8: Fast exchange tip |
| 9: Guiding wire |
| 10: Stepping motor |
| 11: Optical fiber array connector |
| 12: First high-speed optical switch |
| 13: Optical delay line array |
| 14: Light source |
| 15: Interferometer |
| 16: Photodetector |
| 17: Data acquisition card |
| 18: Imaging host |
| 19: Image processor and display terminal |
| 20: Closed-loop monitoring device for retracement |
| 21: Optical fiber bundle |
| 22: Second high-speed optical switch |

SPECIFIC EMBODIMENTS

In order to make the technical means of the present invention more clear and understandable to the extent that those skilled in the art may implement them in accordance with the content of the description, and to make the above-mentioned objectives, features and advantages of the present invention more obvious and understandable, the particular embodiments of the present invention will be described in more detail below with reference to the accompanying drawings.

It should be noted that, certain words are used in the specification and claims to refer to specific components. Those skilled in the art should understand that, they may use different terms to refer to the same component. This specification and claims use the difference in function of the components as the criterion for distinguishing, instead of using the difference in the terms as a way to distinguish the components. For example, "comprise/include" or "comprising/including" mentioned in the entire specification and claims is an open term, it should be interpreted as "including but not limited to". The following description of the specification are preferred embodiments for implementing the present invention, but the description is based on the general principles of the specification and is not intended to limit the scope of the present invention. The protection scope of the present invention shall be subject to those defined by the appended claims.

Figure 1A:
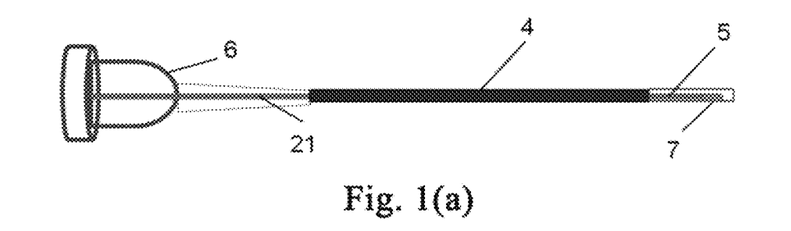
FIG. 1(a) is a schematic diagram showing the structure of an MLA-OCT imaging catheter according to a particular embodiment of the present invention.

FIG. 1(a) is a schematic diagram showing the structure of an MLA-OCT imaging catheter 3 according to a particular embodiment of the present invention, the MLA-OCT imaging catheter 3 comprises an inner tube 5, an outer tube 4, and a multi-core catheter connector 6; wherein the inner tube 5 is located inside the outer tube 4 and comprises an optical fiber bundle 21 and a microlens array 7 at the distal end, the optical fiber bundle 21 comprises two or more optical fibers, and the microlens array 7 comprises two or more microlenses; the proximal end of the outer tube 4 is connected to a retracement controller 2 through the multi-core catheter connector 6, and the distal end of the outer tube 4 enters a lumen in human body.

In a particular embodiment, the optical fiber bundle 21 is a high-density optical fiber bundle, and the multi-core catheter connector 6 is a high-density multi-core catheter connector.

In a particular embodiment, the microlens array 7 is a high-density microlens array, and the microlens may be selected from a spherical lens, a cylindrical lens, or a silicon lens.

In a particular embodiment, the multi-core catheter connector 6 is provided with anti-slip lines.

In a particular embodiment, the distal end of the outer tube 4 is also provided with a transparent imaging window and a quick exchange tip 8, and the quick exchange tip 8 is provided with a developing ring. The transparent imaging window has a high transmittance to the light of a specific wavelength band, and mainly has the function of transmitting light; the developing ring cannot be penetrated by X-rays, and with the help of its function, the exact position of the catheter in the body may be shown.

Figure 1B:
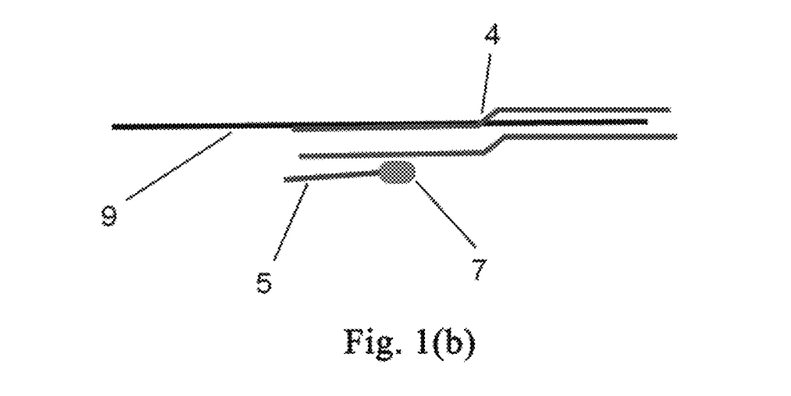
FIG. 1(b) is a schematic diagram showing the quick exchange tip of an MLA-OCT imaging catheter according to a particular embodiment of the present invention.

FIG. 1(b) is a schematic diagram showing the structure of the quick exchange tip 8 of an MLA-OCT imaging catheter 3 according to a particular embodiment of the present invention, wherein the quick exchange tip 8 has a guiding wire inlet, and the guiding wire 9 is put into the quick exchange tip 8, and the MLA-OCT imaging catheter 3 may be pushed along the guiding wire 9 to the target lesion area in the patient's lumen.

Figure 2:
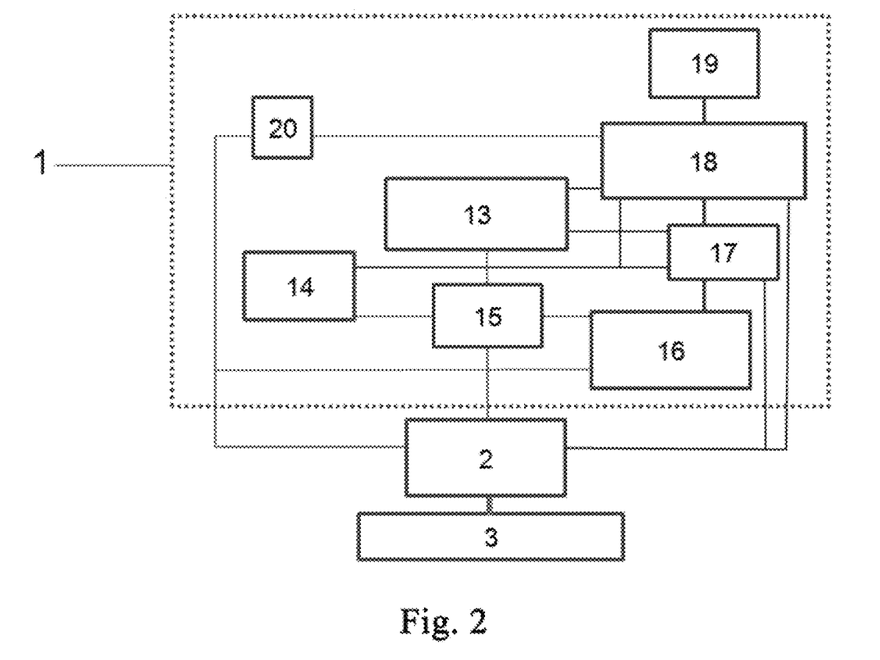
FIG. 2 is a schematic diagram showing an MLA-OCT imaging system according to a particular embodiment of the present invention.

FIG. 2 is a schematic diagram showing an MLA-OCT imaging system according to a particular embodiment of the present invention, the MLA-OCT imaging system comprises: a host equipment 1, an MLA-OCT imaging catheter 3, and a retracement controller 2; wherein the host equipment 1 comprises a light source 14, an interferometer 15, a photodetector 16, a data acquisition card 17, an imaging host 18, an image processor and a display terminal 19, and so on. The retracement controller 2 and the MLA-OCT imaging catheter 3 are located on the signal arm of the interferometer 15, and the reference arm of the interferometer 15 is provided with an optical delay line array 13. The proximal end of the retracement controller 2 is connected to the interferometer 15, and the distal end is connected to the MLA-OCT imaging catheter 3. The left side of the interferometer 15 is connected to the light source 14, the right side is connected to the photodetector 16, and the output end of the photodetector 16 is connected to the data acquisition card 17, the output end of the data acquisition card 17 is connected to the imaging host 18, and the output end of the imaging host 18 is connected to the image processor and the display terminal 19.

Wherein the light source 14 is divided into a beam of sample light and a beam of reference light by the interferometer 15; the sample light enters a signal arm to reach human tissue, while the reference light enters a reference arm to reach an optical delay line of the interferometer 15, the multi-point backscattered light of the human tissue collected by the MLA-OCT imaging catheter 3 is a set of scanning optical signals, wherein each single-point scattered light is a first optical signal, i.e., the scanning optical signal is a collection of the first optical signals of each single point; and the light returned by the optical delay line is a second optical signal. The first optical signal returns to the interferometer 15 via the signal arm, and the second optical signal returns to the interferometer 15 via the reference arm. When the first optical signal and the second light interfere in the interferometer 15, the generated optical interference signal is detected by the photodetector 16. The photodetector 16 receives the optical interference signal and converts it into an electrical signal to output to the data acquisition card 17. The card 17 converts the automatically collected electrical signal into a digital signal, and the digital signal is stored in the imaging host 18, then the imaging host 18 analyzes and processes the digital signal, thereby obtaining corresponding images in the image processor and the display terminal 19. The data processing device generates a two-dimensional cross-section image of the lumen in human tissue according to the interference signals of all single points, and then the retracement controller 2 activates the MLA-OCT imaging catheter 3 to move axially for axial scanning, thereby generating a three-dimensional image of human tissue; wherein the interference may only occur when the optical paths of the reference arm and the sample arm match within the coherence length of the light source 14.

In a particular embodiment, the MLA-OCT imaging system further comprises a closed-loop monitoring device for retracement 20, which is electrically connected to the retracement controller 2, the photodetector 16, and the imaging host 18, so as to form the closed-loop control of the retracement of the MLA-OCT imaging catheter 3 and prevent the occurrence of forced retracement of the imaging catheter.

In a particular embodiment, the light source 14 may be a high-coherence light source such as a laser, or a low-coherence light source such as a superluminescent diode.

In a particular embodiment, the optical delay line array 13 is a high-density optical delay line array.

Figure 3A:
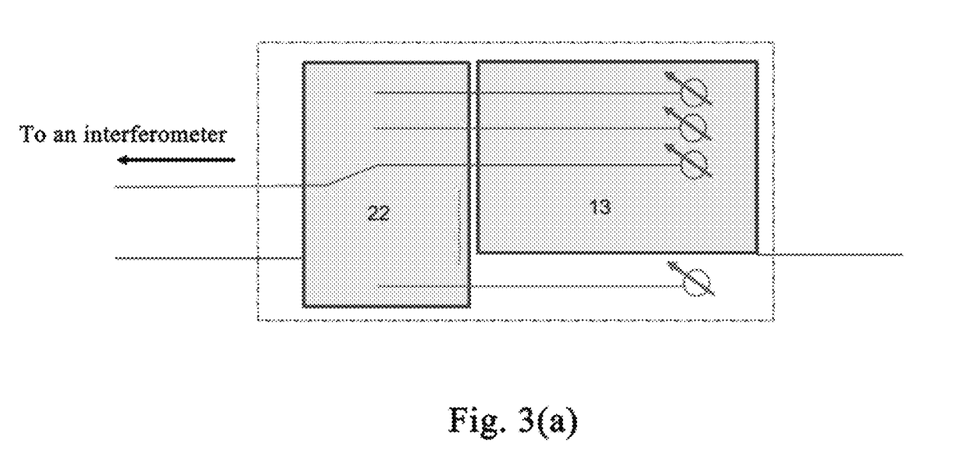
FIG. 3(a) is a schematic diagram showing the structure of the reference arm of the interferometer in an MLA-OCT imaging system according to a particular embodiment of the present invention.

FIG. 3(a) is a schematic diagram showing the structure of the reference arm of the interferometer 15 in an MLA-OCT imaging system according to a particular embodiment of the present invention, wherein the reference arm is provided with a second high-speed optical switch 22 and an optical delay line array 13 comprising two or more optical delay lines.

In a particular embodiment, the optical fiber bundle 21 comprises N (N is an integer greater than 1) optical fibers, the second high-speed optical switch 22 is a 1×N high-speed optical switch, and the optical delay line array 13 comprises N optical delay lines. The 1×N high-speed optical switch is a functional switch with the function of switching optical paths, wherein 1 represents the number of input optical signal channels, N represents the number of output optical signal channels, and 1×N represents that the input signal from 1 channel may be switched to N output signal channels.

In an alternative embodiment, if the adjustment speed of the optical delay line may exceed the speed of the second high-speed optical switch 22, only one optical delay line may be provided, and the second high-speed optical switch 22 does not need to be provided, thereby simplifying the configuration of the reference arm.

Figure 3B:
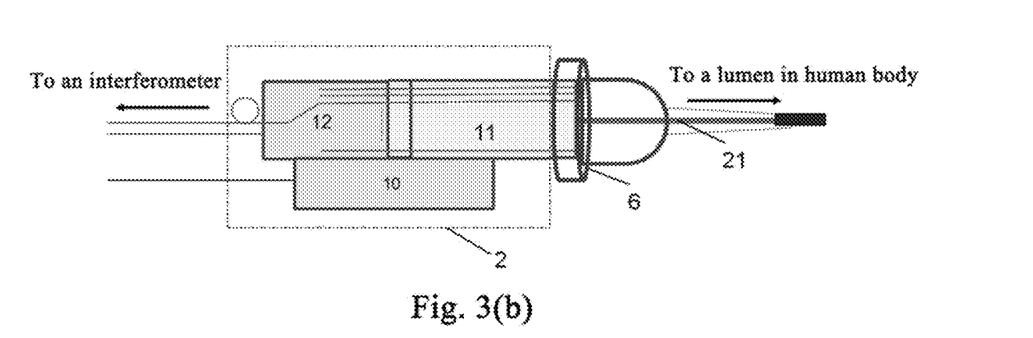
FIG. 3(b) is a schematic diagram showing the structure of the signal arm of the interferometer in an MLA-OCT imaging system according to a particular embodiment of the present invention.

FIG. 3(b) is a schematic diagram showing the structure of the signal arm of the interferometer 15 in an MLA-OCT imaging system according to a particular embodiment of the present invention. As shown in the figure, the retracement controller 2 located on a signal arm comprises: a stepping motor 10, a first high-speed optical switch 12, an optical fiber bundle 21 and an optical fiber array connector 11; wherein the proximal end of the retracement controller 2 is connected to the interferometer 15, and the optical fiber array connector 11 at the distal end of the retracement controller 2 is connected to a multi-core catheter connector 6, so that the retracement controller 2 is connected to an MLA-OCT imaging catheter 3.

In a particular embodiment, the optical fiber bundle 21 comprises N (N is an integer greater than 1) optical fibers, the first high-speed optical switch 12 is a 1×N high-speed optical switch, and the optical fiber array connector 11 is an N-optical fiber array connector.

Figure 4:
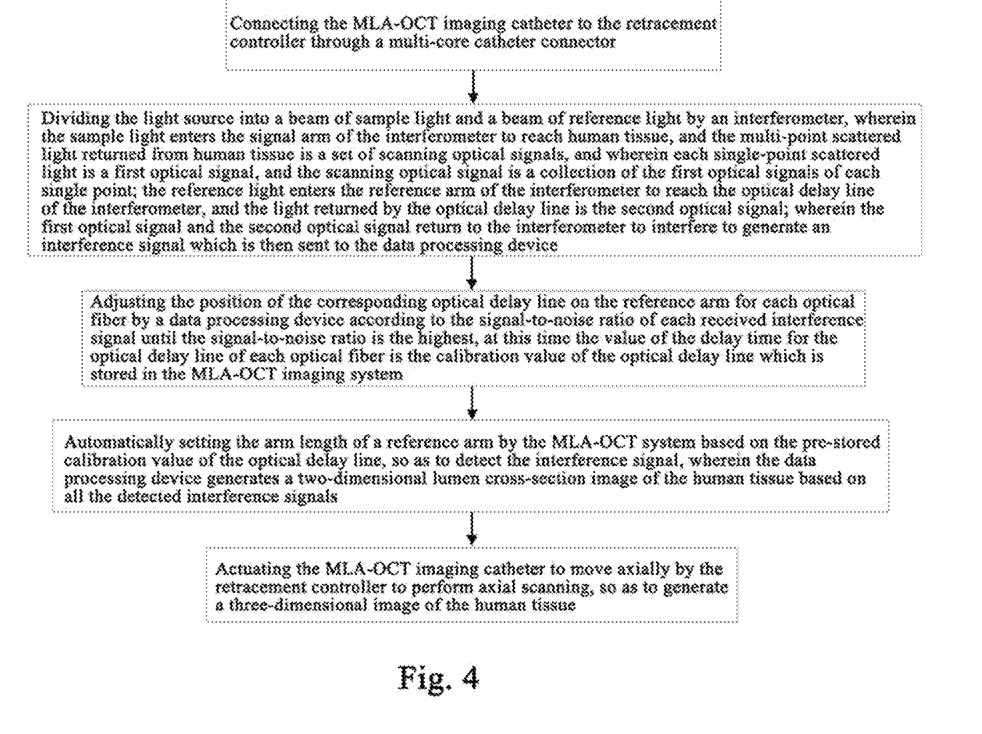
FIG. 4 is a schematic diagram showing the steps of an MLA-OCT imaging method according to a particular embodiment of the present invention.

FIG. 4 is a schematic diagram showing the steps of an MLA-OCT imaging method according to a particular embodiment of the present invention. As shown in the figure, the MLA-OCT imaging method includes the following steps:

S1: connecting the MLA-OCT imaging catheter 3 to the retracement controller 2 through a multi-core catheter connector 6, to be ready for calibration;

S2: dividing the light source 14 into a beam of sample light and a beam of reference light by an interferometer 15, wherein the sample light enters the signal arm of the interferometer 15 to reach human tissue, and the multi-point scattered light returned from human tissue and collected by the MLA-OCT imaging catheter is a set of scanning optical signals, and wherein each single-point scattered light is a first optical signal, and the scanning optical signal is a collection of the first optical signals of each single point; the reference light enters the reference arm of the interferometer 15 to reach the optical delay line of the interferometer 15, and the light returned by the optical delay line is the second optical signal; wherein the first optical signal and the second optical signal return to the interferometer 15 for coherent detection to generate an interference signal which is then sent to the data processing device;

S3: adjusting the position of the corresponding optical delay line on the reference arm for each optical fiber by a data processing device according to the signal-to-noise ratio of each received interference signal until the signal-to-noise ratio of the interference signal is the highest, at this time the value of the delay time for the optical delay line of each optical fiber is the calibration value of the optical delay line which is stored in the MLA-OCT imaging system;

S4: automatically setting the arm length of the reference arm by the MLA-OCT system based on the pre-stored calibration value of the optical delay line, so as to detect the interference signal, wherein the imaging host 18 generates a two-dimensional lumen cross-section image of the human tissue based on all the detected interference signals;

S5: actuating the MLA-OCT imaging catheter 3 to move axially by the retracement controller 2 to perform axial scanning, then a series of two-dimensional lumen cross-section images of the human tissue are generated by the imaging host 18, thereby obtaining a three-dimensional image of the human tissue.

In a particular embodiment, step S1 is: inserting a multi-core catheter connector 6 at the proximal end of the MLA-OCT imaging catheter 3 into the optical fiber array connector 11 on the retracement controller 2 to be ready for calibration;

In a particular embodiment, step S3 is: the first high-speed optical switch 12 and the second high-speed optical switch 22 are both 1×N high-speed optical switches, and the two are synchronously driven, i.e., the first output signal channel of the first high-speed optical switch 12 and the first output signal channel of the second high-speed optical switch 22 are opened synchronously, and the second output signal channel of the first high-speed optical switch 12 and the second output signal channel of the second high-speed optical switch 22 are opened synchronously, by analogy, the Nth output signal channel of the first high-speed optical switch 12 and the Nth output signal channel of the second high-speed optical switch 22 are opened synchronously. The position M of each two corresponding output signal channels corresponds to a microlens M in the microlens array at the tip of the inner tube 5 of the MLA-OCT imaging catheter 3, an optical fiber M in the optical fiber bundle 21 and the optical fiber array connector 11, an optical delay line M of the optical delay line array 13, wherein the imaging host 18 adjusts the position of the optical delay line M according to the signal-to-noise ratio of the received interference signal and the imaging quality until the signal-to-noise ratio is the highest and the imaging quality is the best; at this time the value of the delay time for the optical delay line M is set as the calibration value CV-M of the microlens M/optical fiber M/optical delay line M of the MLA-OCT imaging catheter 3. The output signal channels of the first high-speed optical switch 12 are opened from 1 to N, and the output signal channels of the second high-speed optical switch 22 are also opened synchronously from 1 to N, and the calibration values CV-1, CV-2, . . . , CV-N corresponding to all lenses/fibers/optical delay lines are obtained; all optical delay lines are set at their calibration values, and the calibration values are stored in the MLA-OCT imaging system.

In an optional embodiment, if the adjustment speed of the optical delay line may exceed the speed of the second high-speed optical switch 22, one optical delay line may be used to correspond to N microlenses/N optical fibers in real time, and the reference arm does not need to be provided with a second high-speed optical switch 22. At this time, step S3 is: adjusting the position of the optical delay line on the reference arm by the data processing device according to the signal-to-noise ratio of the received interference signal until the signal-to-noise ratio is the highest, at this time the value of the delay time for the optical delay line is the calibration value of the optical delay line. The same as the above operation, for each optical fiber, the position adjustment of the optical delay line is respectively performed once, so as to obtain the calibration value of the corresponding optical delay line, finally N calibration values of the optical delay lines corresponding to N lenses/N optical fibers are stored in the MLA-OCT imaging system.

In a particular embodiment, step S4 is: sending the MLA-OCT imaging catheter 3 along the PCI guiding catheter and the guiding wire 9 to a site of 5 mm-10 mm away from the distal end of the luminal lesion, and automatically setting the arm length of the reference arm by the MLA-OCT system based on the pre-stored calibration value of the optical delay line; subsequently, if the lumen is blood vessel, a contrast agent is injected to flush out the blood, and the MLA-OCT imaging catheter 3 starts to retreat while imaging; if it is a nonvascular lumen, the MLA-OCT imaging catheter 3 may directly retreat while imaging. During imaging, the MLA-OCT imaging catheter 3 does not need to make any rotational movement, wherein the first high-speed optical switch 12 and the second high-speed optical switch 22 are both 1×N high-speed optical switches, and the emission and collection of the first optical signal and the second optical signal are performed by the synchronously driven first high-speed optical switch 12 and the second high-speed optical switch 22, sequentially connecting the microlens M at the distal end of the inner tube 5, the optical fiber M in the optical fiber bundle 21, and the optical delay line M in the optical delay line array 13. The output signal channel of the first high-speed optical switch 12 and the output signal channel of the second high-speed optical switch 22 are opened synchronously from 1 to N to obtain N the first optical signals of the scanned human tissues, i.e., a set of scanning optical signals, so that the imaging host 18 generates a two-dimensional lumen cross-section image. Subsequently, in step S5, the retracement controller 2 actuates the MLA-OCT imaging catheter 3 to move axially for axial scanning, then a series of two-dimensional lumen cross-section images of the human tissue are generated by the imaging host 18, thereby obtaining a three-dimensional image of the human tissue.

Although the embodiments of the present invention are described above with reference to the accompanying drawings, the present invention is not limited to the above particular embodiments and application fields. The above particular embodiments are only illustrative, instructive, and not restrictive. Under the enlightenment of this specification and without departing from the scope of protection of the claims of the present invention, those of ordinary skill in the art may also make many modifications, which all belong to the protection scope of the present invention.

The invention claimed is:

1. A microlens array optical coherence tomography (MLA-OCT) imaging catheter, comprising an inner tube, an outer tube and a multi-core catheter connector, wherein
    the inner tube is located inside the outer tube;
    the inner tube comprises an optical fiber bundle and a microlens array, the optical fiber bundle comprises two or more optical fibers, the microlens array comprises two or more microlenses, and the microlens array is located at a distal end of the optical fiber bundle;
    a proximal end of the outer tube is connected to a retracement controller for driving a retracement of the MLA-OCT imaging catheter through a multi-core catheter connector;
    a signal arm of an interferometer is provided with the retracement controller and the MLA-OCT imaging catheter;
    the retracement controller comprises a first high-speed optical switch, and a reference arm of the interferometer is provided with a second high-speed optical switch and an optical delay line array comprising an optical delay line;
    a light source is divided into a beam of sample light and a beam of reference light by the interferometer, wherein the sample light enters the signal arm of the interferometer to reach a human tissue, and a multi-point scattered light returned from the human tissue and collected by the MLA-OCT imaging catheter is a set of scanning optical signals, wherein each single-point of scattered light is a first optical signal; and wherein the reference light enters the reference arm of the interferometer to reach the optical delay line, and the light returned by the optical delay line is a second optical signal;
    the first high-speed optical switch and the second high-speed optical switch are both 1×N high-speed optical switches, and the two are synchronously driven, sequentially connecting the two or more microlenses in the microlens array, the two or more optical fibers in the optical fiber bundle, and the N optical delay lines in the optical delay line array; and
    an output signal channel of the first high-speed optical switch and an output signal channel of the second high-speed optical switch are opened synchronously from 1 to N to obtain N first optical signals of the human tissue.

2. The MLA-OCT imaging catheter according to claim 1, wherein a distal end of the outer tube is provided with a quick exchange tip, and the quick exchange tip is provided with a developing ring and a guiding wire inlet and outlet.

3. The MLA-OCT imaging catheter according to claim 1, wherein a distal end of the outer tube is provided with a transparent imaging window.

4. The MLA-OCT imaging catheter according to claim 1, wherein the multi-core catheter connector is provided with anti-slip lines.

5. An MLA-OCT imaging system, comprising: a host equipment, and the MLA-OCT imaging catheter according to claim 1, wherein:
    the host equipment comprises an optical device and a data processing device, the optical device comprises the light source and the interferometer; the signal arm of the interferometer is provided with the retracement controller and the MLA-OCT imaging catheter, and the reference arm of the interferometer is provided with the optical delay line array comprising the optical delay line; the light source is divided into the beam of sample light and the beam of reference light by the interferometer, the sample light enters the signal arm of the interferometer to reach the human tissue, and the multi-point scattered light returned from the human tissue and collected by the MLA-OCT imaging catheter is the set of scanning optical signals, wherein each single-point of scattered light is the first optical signal, and the scanning optical signal is a collection of the first optical signals of each single point; the reference light enters the reference arm of the interferometer to reach the optical delay line of the interferometer, and the light returned by the optical delay line is the second optical signal; wherein the first optical signal and the second optical signal return to the interferometer to interfere to generate an interference signal which is then sent to the data processing device;
    the retracement controller comprises a stepping motor, the first high-speed optical switch, an optical fiber bundle, and an optical fiber array connector; a proximal end of the retracement controller is connected to the interferometer, and a distal end is connected to the MLA-OCT imaging catheter through the multi-core catheter connector, the MLA-OCT imaging catheter is activated by the retracement controller to move axially to perform axial scanning, so as to generate a three-dimensional image of the tissue.

6. The MLA-OCT imaging system according to claim 5, wherein the data processing device comprises: a photodetector, a data acquisition card, an imaging host, an image processor, and a display terminal.

7. The MLA-OCT imaging system according to claim 5, wherein the host equipment comprises a closed-loop monitoring device for retracement.

8. The MLA-OCT imaging system according to claim 5, wherein the optical delay line array comprises two or more optical delay lines.

9. A method for calibrating the MLA-OCT imaging catheter in the MLA-OCT imaging system according to claim 5, including: after connecting the MLA-OCT imaging catheter comprising the optical fiber bundle to the retracement controller, adjusting a position of a corresponding optical delay line on the reference arm for each optical fiber by the data processing device according to a signal-to-noise ratio of the received interference signal until the signal-to-noise ratio is the highest, and taking the value of a delay time for the optical delay line of each optical fiber as a calibration value of the optical delay line.

10. An MLA-OCT imaging method using the MLA-OCT imaging system according to claim 5, which includes the following steps:
connecting the MLA-OCT imaging catheter to the retracement controller through the multi-core catheter connector;
dividing the light source into the beam of sample light and the beam of reference light by the interferometer, wherein the sample light enters the signal arm of the interferometer to reach the human tissue, and the multi-point scattered light returned from the human tissue and collected by the MLA-OCT imaging catheter is the set of scanning optical signals, and wherein each single-point scattered light is the first optical signal, and the scanning optical signal is the collection of the first optical signals of each single point; the reference light enters the reference arm of the interferometer to reach the optical delay line of the interferometer, and the light returned by the optical delay line is the second optical signal; wherein the first optical signal and the second optical signal return to the interferometer to interfere to generate the interference signal which is then sent to the data processing device;
adjusting a position of the corresponding optical delay line on the reference arm for each optical fiber by the data processing device according to a signal-to-noise ratio of each received interference signal until the signal-to-noise ratio is the highest, and taking the value of a delay time for the optical delay line of each optical fiber as a calibration value of the optical delay line which is stored in the MLA-OCT imaging system;
automatically setting the arm length of the reference arm by the MLA-OCT system based on a pre-stored calibration value of the optical delay line, so as to detect the interference signal, wherein the data processing device generates a two-dimensional lumen cross-section image of the human tissue based on all the detected interference signals; and
actuating the MLA-OCT imaging catheter to move axially by the retracement controller to perform axial scanning, so as to generate a three-dimensional image of the human tissue.

* * * * *